United States Patent
Lee et al.

(10) Patent No.: US 10,405,735 B2
(45) Date of Patent: Sep. 10, 2019

(54) TOWING DEVICE FOR ENDOSCOPY

(71) Applicant: AJOU UNIVERSITY INDUSTRY—ACADEMIC COOPERATION FOUNDATION, Suwon-si, Gyeonggi-do (KR)

(72) Inventors: Moon Gu Lee, Gwacheon-si (KR); Chang Ho Jung, Seoul (KR); Yong Ho Jeon, Suwon-si (KR); Yun Ho Jung, Seoul (KR)

(73) Assignee: AJOU UNIVERSITY INDUSTRY-ACADEMIC COOPERATION FOUNDATION, Suwon-si (KR)

( * ) Notice: Subject to any disclaimer, the term of this patent is extended or adjusted under 35 U.S.C. 154(b) by 265 days.

(21) Appl. No.: 15/455,952

(22) Filed: Mar. 10, 2017

(65) Prior Publication Data
US 2017/0258301 A1   Sep. 14, 2017

(30) Foreign Application Priority Data

Mar. 11, 2016 (KR) .................. 10-2016-0029887

(51) Int. Cl.
*A61B 1/00* (2006.01)
*A61B 1/04* (2006.01)
(Continued)

(52) U.S. Cl.
CPC ...... *A61B 1/00158* (2013.01); *A61B 1/00121* (2013.01); *A61B 1/00131* (2013.01);
(Continued)

(58) Field of Classification Search
CPC ... A61B 1/00158; A61B 1/04; A61B 1/00121; A61B 1/00131; A61B 17/0218;
(Continued)

(56) References Cited

U.S. PATENT DOCUMENTS

| | | | |
|---|---|---|---|
| 2002/0173805 A1 | 11/2002 | Matsuno et al. | 606/151 |
| 2004/0050395 A1 | 3/2004 | Ueda et al. | 128/899 |
| 2007/0135678 A1 | 6/2007 | Suzuki | 600/37 |

FOREIGN PATENT DOCUMENTS

| | | |
|---|---|---|
| JP | 2007-167400 A | 7/2007 |
| JP | 2008-62004 A | 3/2008 |
| JP | 2012-115386 A | 6/2012 |
| KR | 10-2011-0071976 A | 6/2011 |
| KR | 10-2014-0049724 A | 4/2014 |

OTHER PUBLICATIONS

JP 2012-115386, Translation of Foreign Patent Document. (Year: 2012).*

(Continued)

*Primary Examiner* — Timothy J Neal
(74) *Attorney, Agent, or Firm* — Stein IP, LLC

(57) ABSTRACT

A towing device for endoscopy including a connecting portion connected to a wire of an endoscope to be moved, wherein a body of the connecting portion is broken when a set amount of tension or more is applied to the connecting portion; a guide portion including an inner path through which the connecting portion moves; a clip portion positioned at an opposite direction of the wire with respect to the guide portion and hooked by the connecting portion to be closed and grip body tissues; and an extension portion configured to move together with the guide portion and having a magnetic force.

8 Claims, 22 Drawing Sheets

(51) Int. Cl.
  *A61B 17/02*  (2006.01)
  *A61B 17/08*  (2006.01)
  *A61B 17/122*  (2006.01)
  *A61B 17/00*  (2006.01)
  *A61B 90/00*  (2016.01)
(52) U.S. Cl.
  CPC ............ *A61B 1/04* (2013.01); *A61B 17/0218* (2013.01); *A61B 17/083* (2013.01); *A61B 17/1227* (2013.01); *A61B 2017/00269* (2013.01); *A61B 2017/00477* (2013.01); *A61B 2017/00876* (2013.01); *A61B 2017/081* (2013.01); *A61B 2090/037* (2016.02)
(58) Field of Classification Search
  CPC .............. A61B 17/083; A61B 17/1227; A61B 2017/00269; A61B 2017/00477; A61B 2017/00876; A61B 2017/081; A61B 2090/037
  See application file for complete search history.

(56) References Cited

OTHER PUBLICATIONS

Korean Office Action dated Sep. 5, 2016, issued by the Korean Intellectual Property Office in corresponding application KR 10-2016-0029887.
Extended European Search Report dated Jul. 18, 2017, issued to European Application No. 17160125.5.

* cited by examiner

75

TOWING DEVICE FOR ENDOSCOPY

CROSS-REFERENCE TO RELATED APPLICATION

This application claims priority to and the benefit of Korean Patent Application No. 10-2016-0029887, filed on Mar. 11, 2016, the disclosure of which is incorporated herein by reference in its entirety.

BACKGROUND

1. Field of the Invention

The present invention relates to a towing device for endoscopy, and more particularly, to a towing device for endoscopy configured to facilitate an initial towing operation of body tissues of a patient by coupling a magnetic material to a portion which grips the body tissues.

2. Discussion of Related Art

Generally, an endoscope is a medical device which observes an inside of the body. Endoscopes are classified according to a part to be examined and a method of viewing the part, and include a bronchoscope, a gastroscope, a laparoscope, and an anoscope.

Endoscopes include a type having one tube called an autoscope and configured to directly observe organs with the naked eye, a type using a lens system, a type configured to directly insert a camera into an organ, a fiberscope using glass fiber, and the like. A part at which a perforation is formed and a suture is needed is sutured using an endoscopic clip or a surgical thread during endoscopic surgery.

When a perforation greater than the clip is formed, since an operation of suturing the perforation using a method such as surgery from the outside of the body is additionally required conventionally, there is a problem in that an operation time is increased. Therefore, there is a need to overcome this problem.

The related art of the present invention is disclosed in Korean Laid-open Patent Application No. 2014-0049724 (Apr. 28, 2014; title of the invention: Surgical instrument for medical)

SUMMARY OF THE INVENTION

The present invention is directed to a towing device for endoscopy capable of facilitating an initial towing operation of body tissues of a patient by coupling a magnetic material to a portion which grips body tissues.

According to an aspect of the present invention, there is provided a towing device for endoscopy including: a connecting portion connected to a wire of an endoscope to be moved, wherein a body of the connecting portion is broken when a set amount of tension or more is applied to the connecting portion; a guide portion including an inner path through which the connecting portion moves; a clip portion positioned at an opposite direction of the wire with respect to the guide portion and hooked by the connecting portion to be closed and grip body tissues; and an extension portion configured to move together with the guide portion and having a magnetic force.

The connecting portion may include a first body connected to the wire, a second body connected to the clip portion, and a breaking body configured to connect the first body and the second body, wherein the breaking body breaks when a set amount of tension or more is applied to the breaking body.

The guide portion and the extension portion may be formed in a pipe shape, and the connecting portion may sequentially pass through insides of the extension portion and the guide portion and may be connected to the clip portion.

Both sides in a longitudinal direction of the extension portion may have different magnetic polarities form each other.

The extension portion may include a permanent magnet.

A plurality of extension portions, which are identical to the extension portion, may be installed, magnetic poles of the extension portions may be alternately disposed, and the extension portions may be coupled by gravitation.

The clip portion may include a linking hook hooked by the connecting portion and having a hook shape, and a grip portion configured to extend from the linking hook and open in a pincers shape, and hooked by the guide portion so that both ends spaced apart from each other come toward each other.

The towing device for endoscopy may further include a connecting weight member detached from or attached to the extension portion, and configured to tow the clip portion and the body tissues together with the extension portion downward due to a weight of the connecting weight member.

The connecting weight member may include iron or a magnet and be coupled to the extension portion by a magnetic force.

A hole into which the extension portion is inserted may be formed in the connecting weight member, and the extension portion made of a magnetic material may be inserted into the connecting weight member and may be connected to the connecting weight member.

In addition, the connecting weight member may be connected to the extension portion to tow body tissues having an internal lesion downward.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which.

DETAILED DESCRIPTION OF EXEMPLARY EMBODIMENTS

Figure 1:
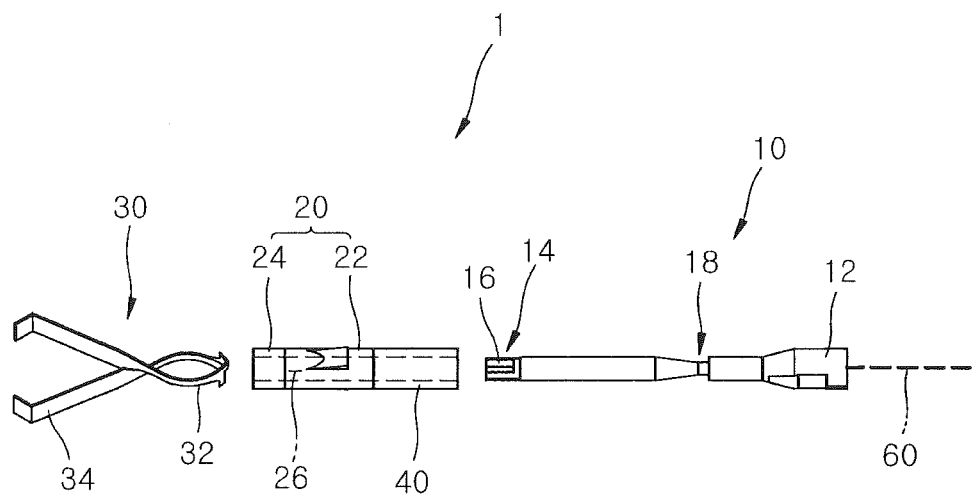
FIG. 1 is a schematic perspective view illustrating a structure of a towing device for endoscopy according to one embodiment of the present invention.

Hereinafter, embodiments of a towing device for endoscopy according to one embodiment of the present invention and a towing method using the same will be described with reference to the accompanying drawings. In the description, thicknesses of lines, sizes of components, and the like illustrated in the drawings may be exaggerated for clarity and convenience of explanation.

In addition, some terms described below are defined in consideration of functions in the present invention, and meanings may vary depending on, for example, a user or operator's intentions or customs. Therefore, the meanings of the terms should be interpreted based on the scope throughout this specification.

Figure 2:
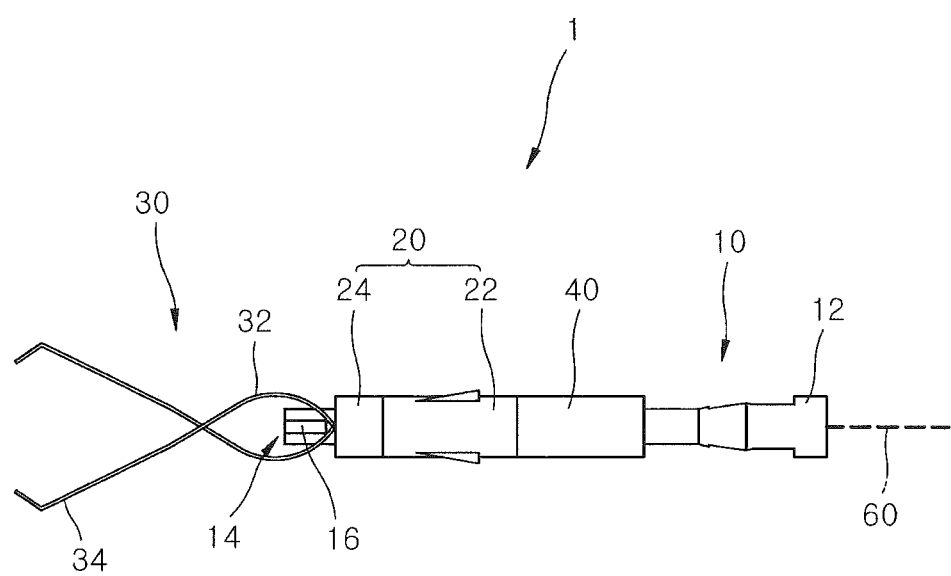
FIG. 2 is a schematic plan view illustrating the towing device for endoscopy according to one embodiment of the present invention.
Figure 3:
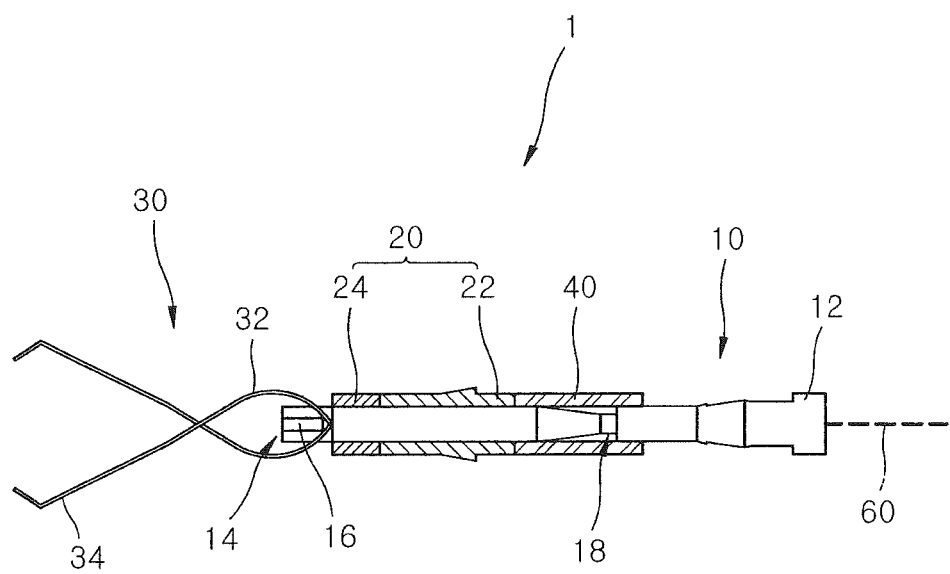
FIG. 3 is a schematic cross-sectional view illustrating the towing device for endoscopy according to one embodiment of the present invention.

FIG. 1 is a schematic perspective view illustrating a structure of a towing device for endoscopy according to one embodiment of the present invention, FIG. 2 is a schematic plan view illustrating the towing device for endoscopy according to one embodiment of the present invention, and FIG. 3 is a schematic cross-sectional view illustrating the towing device for endoscopy according to one embodiment of the present invention.

As illustrated in FIGS. 1 to 3, a towing device 1 for endoscopy according to one embodiment of the present invention includes a connecting portion 10 which is connected to a wire 60 of an endoscope (not shown) to move and in which a body is broken when a set amount of tension or more is applied thereto, a guide portion 20 including an inner path 26 through which the connecting portion 10 moves, a clip portion 30 positioned in an opposite direction of the wire 60 with respect to the guide portion 20 and hooked by the connecting portion 10 to be closed and grip body tissues 70, and an extension portion 40 configured to move together with the guide portion 20 and having a magnetic force.

As illustrated in FIGS. 2 and 3, when the towing device 1 for endoscopy reaches a suture position during an endoscopic procedure, the connecting portion 10 is moved by movement of the wire 60 in a state in which the clip portion 30 positioned in front of the guide portion 20 (at a left side in FIG. 2) is fixed to the connecting portion 10.

Figure 4:
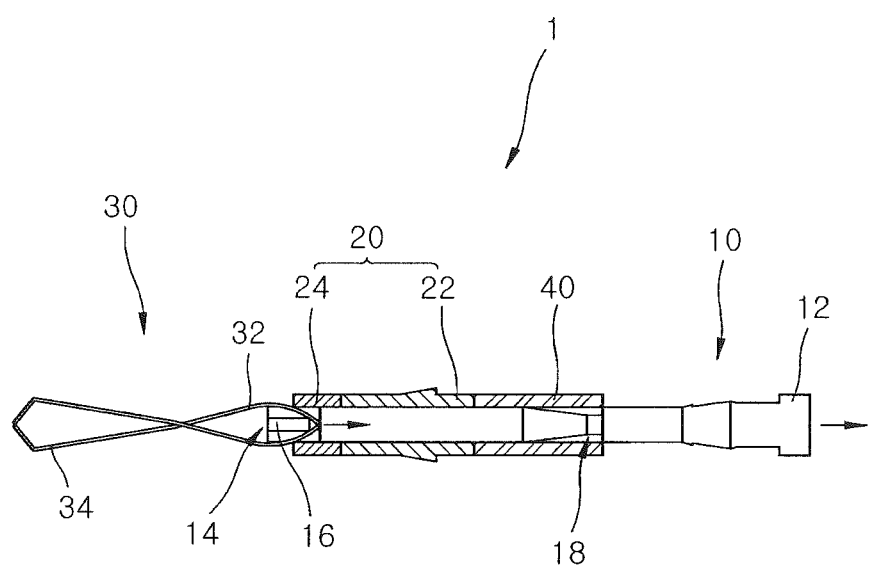
FIG. 4 is a cross-sectional view illustrating a state in which a clip portion according to one embodiment of the present invention moves to an inside of a guide portion along a connecting portion.
Figure 5:
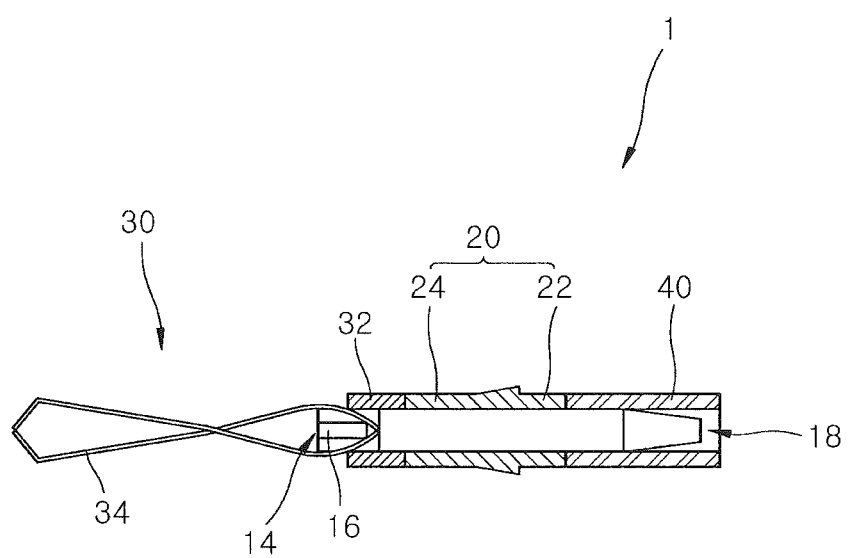
FIG. 5 is a cross-sectional view illustrating a state in which the connecting portion according to one embodiment of the present invention is broken.

FIG. 4 is a cross-sectional view illustrating a state in which a clip portion according to one embodiment of the present invention moves to an inside of a guide portion along a connecting portion, and FIG. 5 is a cross-sectional view illustrating a state in which the connecting portion according to one embodiment of the present invention is broken.

As illustrated in FIG. 4, when the connecting portion 10 is pulled, the metallic clip portion 30 linked to a connecting link 16 of the connecting portion 10 is folded and inserted into the guide portion 20. As illustrated in FIG. 5, when a set amount of tension or more is applied to a breaking body 18, a thin middle portion of the breaking body 18 is disconnected by the tension, and the clip portion 30 is fixed by a fixing ring 24 and a guide body 22.

An endoscope is a useful medical device through which states of internal organs such as a stomach and a large intestine can be viewed. Due to the nature of the endoscope which enters through the mouse or anus, incision is not performed from the outside of the body and various surgical procedures such as examination, diagnosis, sampling, and suturing can be performed using a special tool together with an observation camera. In addition, since internal organs can be accessed without incision from the outside by using the endoscope, recovery is quick after the surgical procedure. However, due to the nature of an endoscopic instrument, a surgical procedure tool has to be made smaller than a predetermined diameter and thin.

In addition, during a suture operation using an endoscope, the clip portion 30 is used. The suture is performed in a manner in which both ends of tissues are hooked by the metallic clip portion 30 and pulled by a strong force to be stuck to each other.

As illustrated in FIGS. 1 and 3, the connecting portion 10 is connected to the wire 60 of the endoscope to be moved, and may be formed in various shapes within a technical idea of a body breaking when a set amount of tension or more is applied thereto. The connecting portion 10 according to one embodiment includes a first body 12, a second body 14, the connecting link 16, and the breaking body 18.

Since the first body 12 is connected to the wire 60, the first body 12 is also moved when the wire 60 moves. Since an external diameter of the first body 12 according to one embodiment is greater than an internal diameter of the guide portion 20, a state in which the first body 12 is not moved into the guide portion 20 and blocked by an outer side of the guide portion 20 is maintained.

The second body 14 may be formed in various shapes within the technical idea of the second body 14 being connected to the clip portion 30 to move into or out of the guide portion 20 together with the clip portion 30. The second body 14 includes the connecting link 16 coupled to a linking hook 32 of the clip portion 30. Since the connecting link 16 protrudes from the second body 14 and a grip portion 34 of the clip portion 30 is linked to the connecting link 16, the clip portion 30 is moved together with the second body 14.

The breaking body 18 is formed in various shapes within the technical idea of the breaking body 18 connecting the first body 12 and the second body 14 and breaking when a set amount of tension or more is applied thereto. The second body 14 is connected to one side of the breaking body 18 (a left side in FIG. 3), and the first body 12 is connected to the other side of the breaking body 18 (a right side in FIG. 3). Since external diameters of the second body 14 and the breaking body 18 are less than an internal diameter of the guide portion 20, the second body 14 and the breaking body 18 are moved along an inner space of the guide portion 20. Since the breaking body 18 includes a portion in which an external diameter is gradually decreased, a portion having a smallest cross-sectional area in a perpendicular direction in the breaking body 18 is broken when a tension is horizontally applied thereto in a lateral direction (see FIG. 3) and the tension is greater than or equal to a set value. Accordingly, the second body 14 is moved together with the wire 60, and the connecting portion 10 excluding the second body 14 is positioned inside the guide portion 20.

The guide portion 20 includes the inner path 26, through which the connecting portion 10 moves, and is fixed to the endoscope. The guide portion 20 according to one embodiment includes the guide body 22 and the fixing ring 24. The guide body 22 and the fixing ring 24 are formed in a pipe shape, and the fixing ring 24 is fixed to one end of the guide body 22 (a left side in FIG. 3). The connecting portion 10 is horizontally moved in a lateral direction along the inner path 26 formed in the guide portion 20.

The clip portion 30 may be formed in various shapes within the technical idea of the clip portion 30 being positioned at an opposite side of the wire 60 with respect to the guide portion 20 and hooked by the connecting portion 10 to be closed and grip the body tissues 70. The clip portion 30 according to one embodiment includes the linking hook 32 and the grip portion 34.

The linking hook 32 has a hook shape to be hooked to the connecting link 16 of the connecting portion 10. When the grip portion 34 extends from the linking hook 32, opens in a pincers shape, and is blocked by the guide portion 20 when the connecting portion 10 moves, and both ends thereof spaced apart from each other come toward each other, the grip portion 34 may grip the body tissues 70.

The extension portion 40 may be formed in various shapes within the technical idea of the extension portion 40 being moved together with the guide portion 20 and has a magnetic force. The guide portion 20 and the extension portion 40 are formed in a pipe shape, and the connecting portion 10 sequentially passes through insides of the extension portion 40 and the guide portion 20, and is connected to the clip portion 30. A permanent magnet may be used for the extension portion 40, and an electromagnet may also be used therefor as necessary.

Figure 6:
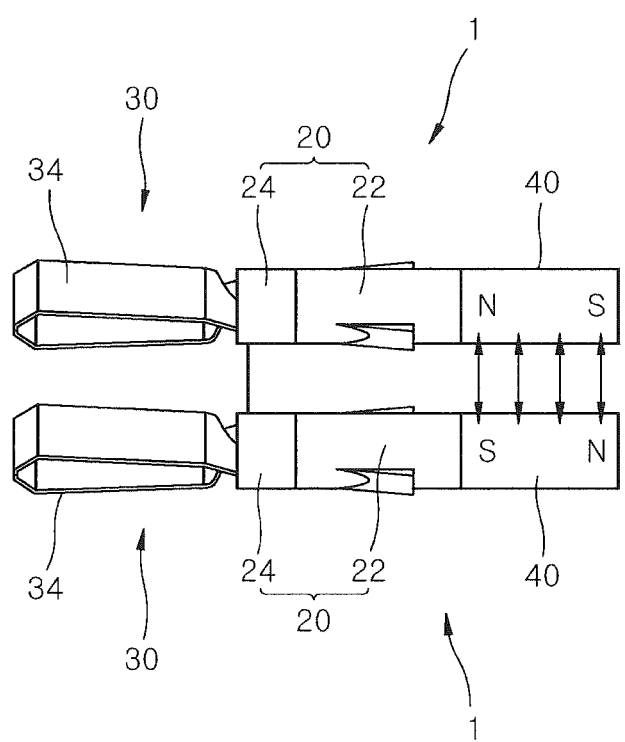
FIG. 6 is a view illustrating a state in which towing devices for endoscopy according to one embodiment of the present invention are sequentially installed in a lateral direction.
Figure 7:
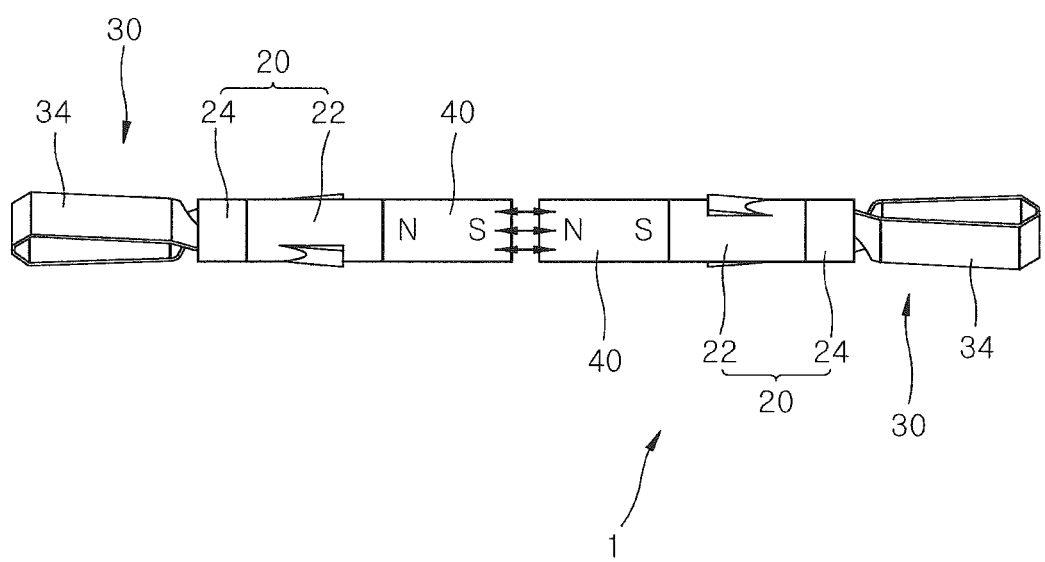
FIG. 7 is a view illustrating a state in which ends of the towing devices for endoscopy according to one embodiment of the present invention face each other.

FIG. 6 is a view illustrating a state in which towing devices for endoscopy according to one embodiment of the present invention are sequentially installed in a lateral direction, and FIG. 7 is a view illustrating a state in which ends of the towing devices for endoscopy according to one embodiment of the present invention face each other.

As illustrated in FIG. 6, when two towing devices 1 for endoscopy are disposed in parallel, both sides of each of adjacent extension portions 40 in a longitudinal direction include magnets having different polarities from each other. That is, when magnetic polarities of the extension portion 40 disposed at one side (an upper portion in FIG. 6) are arranged in an order of an N pole and an S pole, magnetic polarities of the extension portion 40 disposed at the other side (a lower portion in FIG. 6) are arranged in an order of an S pole and an N pole. Accordingly, the extension portion 40 installed at one side and the extension portion 40 installed at the other side are coupled by gravitation. That is, since polarities of the extension portions 40 installed in plurality are disposed to be different from each other, the extension portions 40 are coupled to each other by gravitation.

Since upper and lower extension portions 40 made of magnetic materials have different polarities from each other, the extension portions 40 are not coupled to each other in a different direction.

Figure 8:
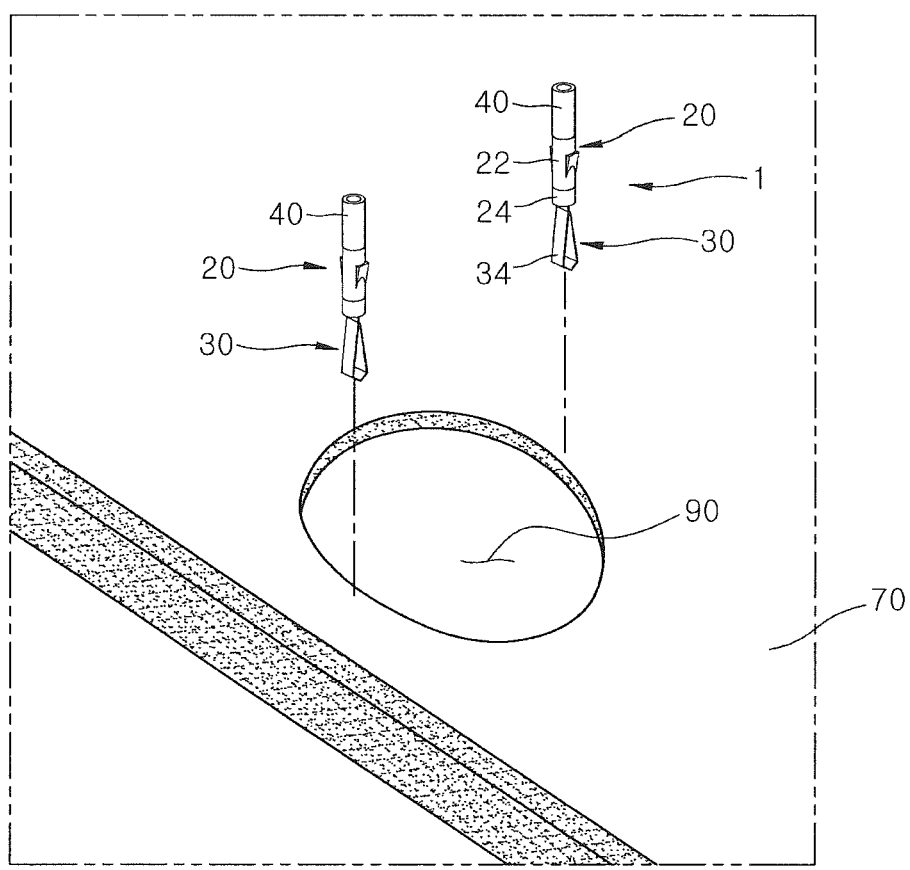
FIG. 8 is a schematic perspective view illustrating a state in which the towing devices for endoscopy are positioned at both sides of a perforation of body tissues.
Figure 9:
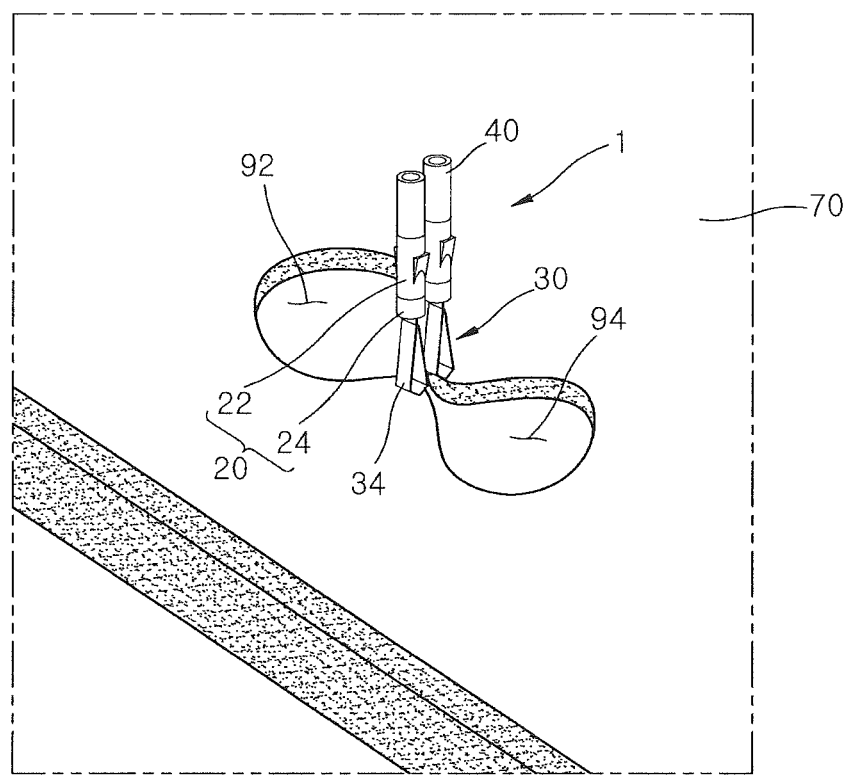
FIG. 9 is a perspective view illustrating a state in which extension portions of the towing devices for endoscopy installed at both sides of the perforation of the body tissues are in contact with each other.

FIG. 8 is a schematic perspective view illustrating a state in which the towing devices for endoscopy are positioned at both sides of a perforation of body tissues, and FIG. 9 is a perspective view illustrating a state in which extension portions of the towing devices for endoscopy installed at both sides of the perforation of the body tissues are in contact with each other.

As illustrated in FIGS. 8 and 9, when two or more towing devices 1 for endoscopy each including the clip portion 30 and the extension portion 40 are installed at two or more positions around a perforation 90, a suture is performed in a manner in which the extension portions 40 are pulled toward each other by magnetic forces. Accordingly, the suture of the large perforation 90 which has conventionally been difficult to perform can be more easily performed.

As illustrated in FIG. 7, when the plurality of towing devices 1 for endoscopy are provided and installed side by side, the extension portions 40 are installed in a shape in which both ends of the extension portions 40 face each other. Here, magnetic polarities of the extension portions 40 facing each other are disposed to be different from each other so that the extension portions 40 are coupled by magnetic forces.

The extension portion 40 made of a magnetic material is coupled to the guide portion 20. The guide portion 20 and the extension portion 40 may be coupled to each other by external surfaces thereof being covered with a thin cover, or the extension portion 40 and the guide portion 20 may be coupled to each other using an adhesive that is harmless to the human body.

Figure 16:
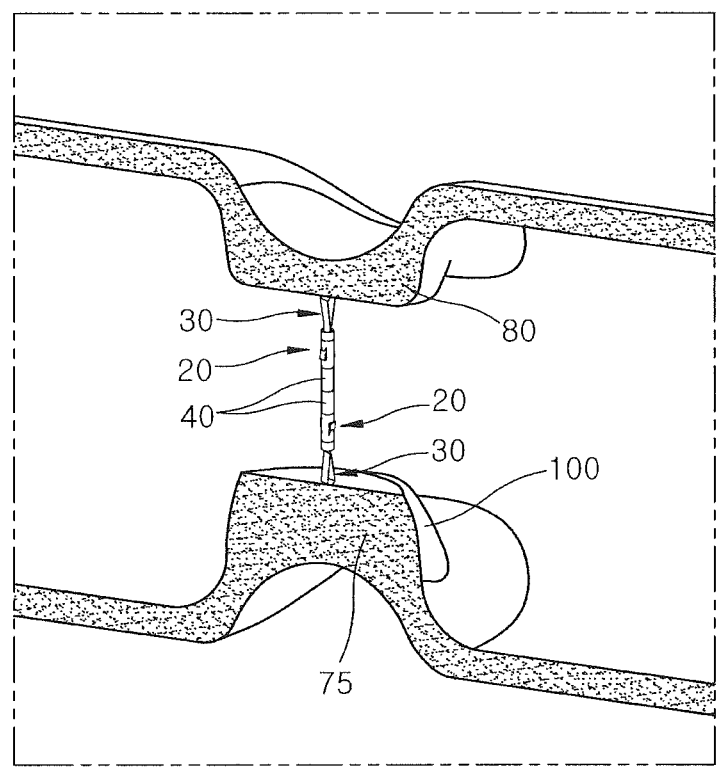
FIG. 16 is a perspective view illustrating a state in which the first body tissues having the internal lesion are towed toward the second body tissues.

FIG. 16 is a perspective view illustrating a state in which the first body tissues having the internal lesion are towed toward the second body tissues.

As illustrated in FIG. 16, when a plurality of towing devices 1 for endoscopy are vertically installed in a row, the towing devices 1 for endoscopy may be applied to towing in which first body tissues 75 having an internal lesion 100 are lifted. Two clip portions 30 and two extension portions 40 are positioned at a position from which the first body tissues 75 are lifted and an opposite position thereof, and the upper and lower extension portions 40 are connected to each other using magnetic forces. Accordingly, during a surgical procedure using the endoscope, the surgical procedure for lifting, examining, and cutting tissues may be more easily performed.

Figure 18:
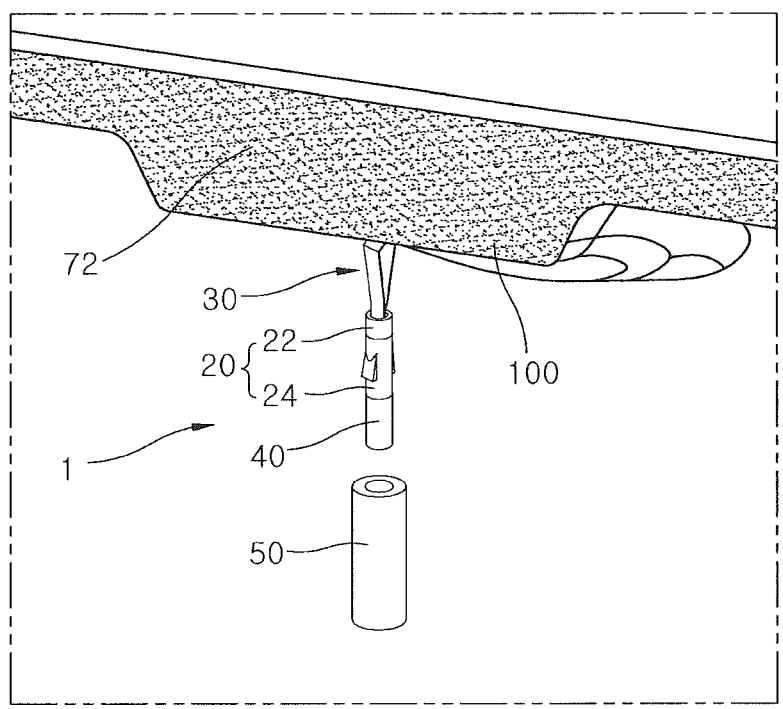
FIG. 18 is a perspective view illustrating a state in which the clip portion, the extension portion, and a connecting weight member are positioned under body tissues having an internal lesion.
Figure 19:
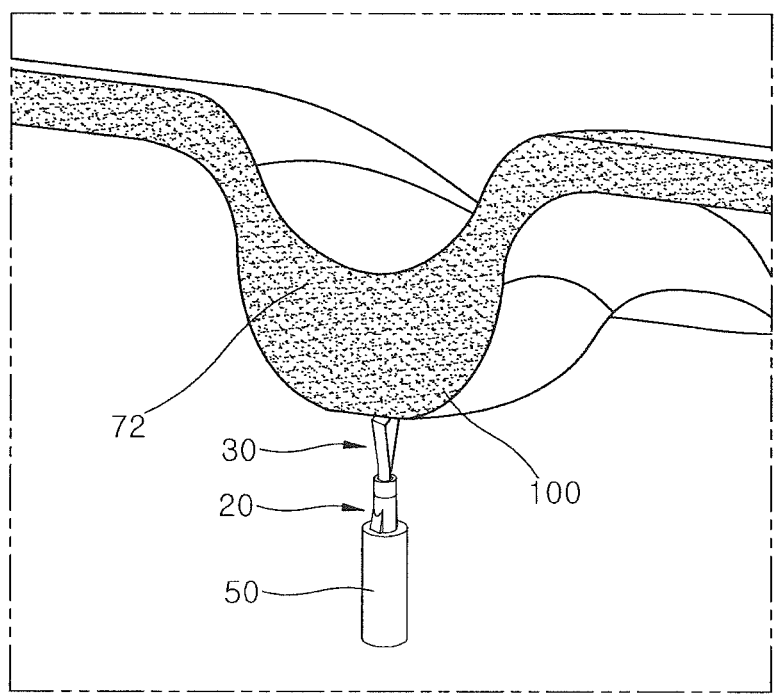
FIG. 19 is a perspective view illustrating a state in which the body tissues having the internal lesion are towed downward by a weight of the connecting weight member.

FIG. 18 is a perspective view illustrating a state in which the clip portion, the extension portion, and a connecting weight member are positioned under body tissues having an internal lesion, and FIG. 19 is a perspective view illustrating a state in which the body tissues having the internal lesion are towed downward by a weight of the connecting weight member.

As illustrated in FIGS. 18 and 19, a connecting weight member 50 is attached to or detached from the extension portion 40, and is used to tow the extension portion 40 together with the clip portion 30 and the body tissues 70 downward using a weight thereof. The connecting weight member 50 according to one embodiment includes iron or a magnet and is coupled to the extension portion 40 by a magnetic force. Since a hole into which the extension portion 40 is inserted is provided in the connecting weight member 50 and the extension portion 40 made of a magnetic material is inserted into the connecting weight member 50, the extension portion 40 is connected to the connecting weight member 50.

The towing device 1 for endoscopy according to one embodiment of the present invention may facilitate an initial towing of the large perforation 90 by coupling the extension portion 40 made of a magnetic material to the clip portion 30 used for an endoscopic procedure. Accordingly, a suturing procedure for the large perforation 90, which is not sutured when only the clip portion 30 is used, may also be performed using the endoscope. In addition, since the towing device 1 for endoscopy having a magnetic force is used, various surgical procedures can also be performed by lifting an inside region of an organ.

The towing device 1 for endoscopy has a type in which the extension portion 40 having a magnetic characteristic is attached to the clip portion 30 for an endoscopic suture, and during an endoscopic procedure using two or more clip portions 30, the clip portions 30 are pulled toward each other by magnetic fields to facilitate a suture or a towing of the body tissues 70.

Hereinafter, a towing method using the towing device 1 for endoscopy according to one embodiment of the present invention will be described in detail with reference to the accompanying drawings.

Figure 10:
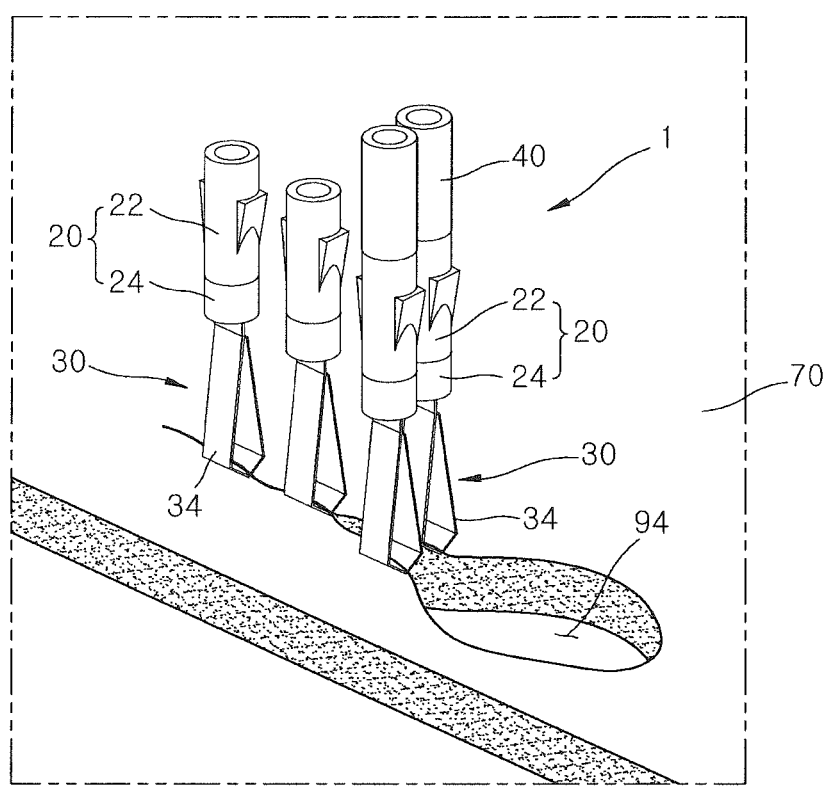
FIG. 10 is a perspective view illustrating a state in which one side of the perforation divided into two portions is primarily sutured by towing devices for endoscopy.
Figure 11:
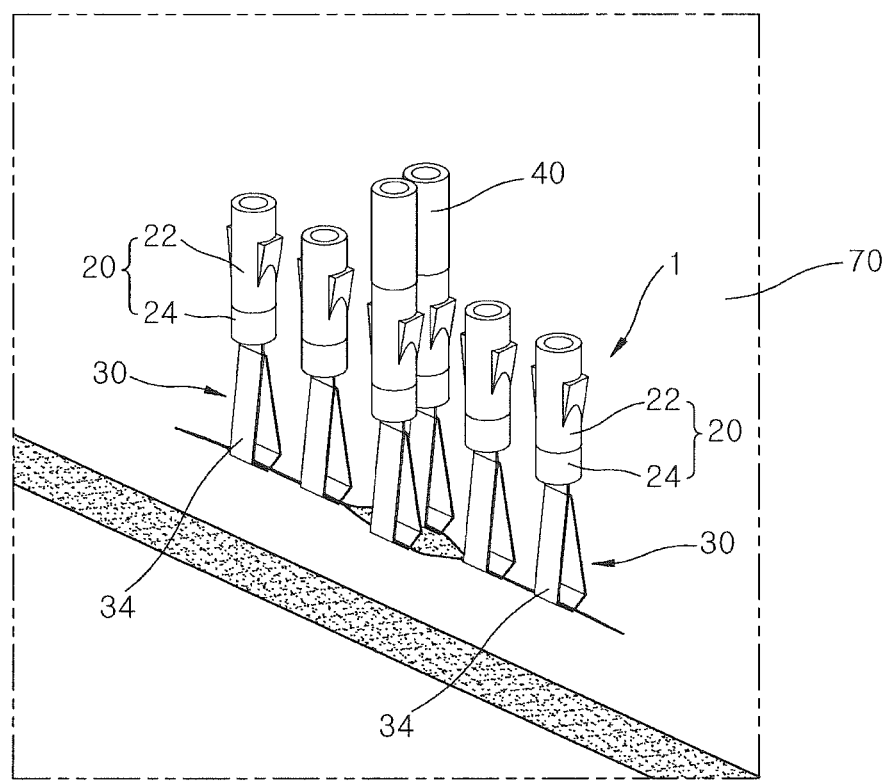
FIG. 11 is a perspective view illustrating a state in which the other side of the perforation divided into two portions is secondarily sutured by towing devices for endoscopy.
Figure 12:
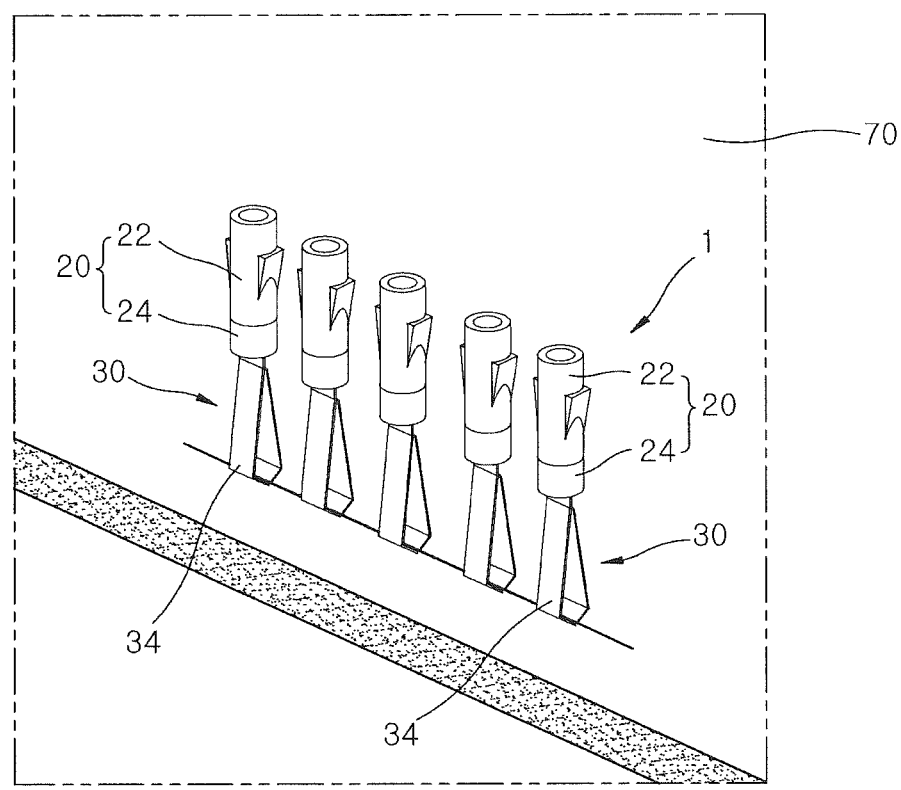
FIG. 12 is a perspective view illustrating a state in which the extension portions made of magnetic materials are removed and the suture is completed.
Figure 20:
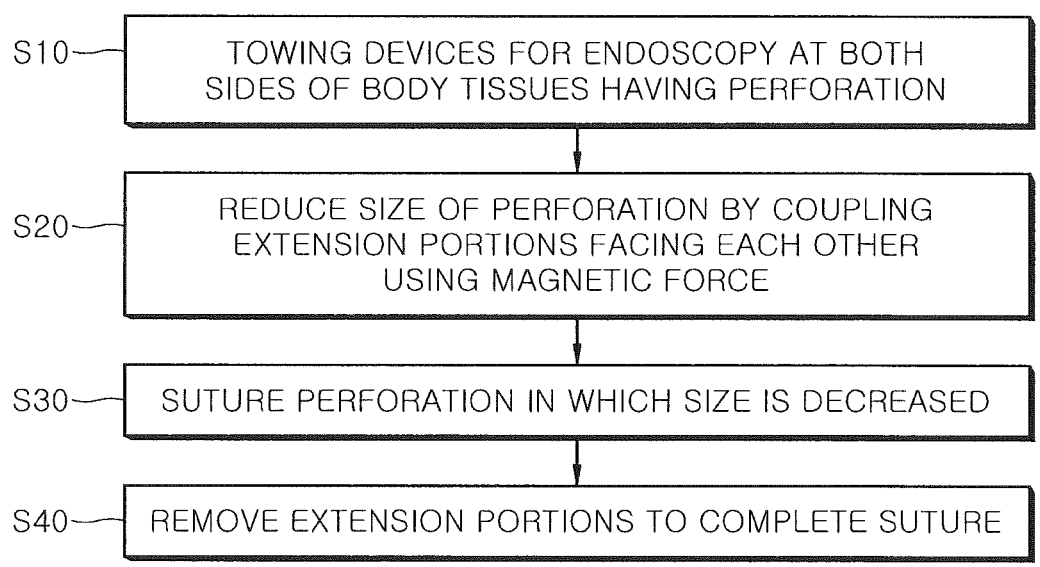
FIG. 20 is a flowchart of a towing method using a towing device for endoscopy according to one embodiment of the present invention.

FIG. 8 is a schematic perspective view illustrating a state in which the towing devices for endoscopy are positioned at both sides of a perforation of body tissues, FIG. 9 is a perspective view illustrating a state in which extension portions of the towing devices for endoscopy installed at both sides of the perforation of the body tissues are in contact with each other, FIG. 10 is a perspective view illustrating a state in which one side of the perforation divided into two portions is primarily sutured by towing devices for endoscopy, FIG. 11 is a perspective view illustrating a state in which the other side of the perforation divided into two portions is secondarily sutured by towing devices for endoscopy, FIG. 12 is a perspective view illustrating a state in which the extension portions made of magnetic materials are removed and the suture is completed, and FIG. 20 is a flowchart of a towing method using a towing device for endoscopy according to one embodiment of the present invention.

As illustrated in FIGS. 8 and 20, towing devices 1 for endoscopy each having the clip portion 30 configured to grip a target object and the extension portion 40 having a magnetic force are installed at both sides of the body tissues 70 in which a perforation 90 is formed (S10). The towing devices 1 for endoscopy to which magnetic materials are coupled are attached to body tissues 70 located at a periphery of the perforation 90 centered on the perforation 90.

As illustrated in FIGS. 9 and 20, after the towing devices 1 for endoscopy are installed at both sides of the body tissues 70 in which the perforation 90 is formed, the extension portions 40 are coupled to each other by the magnetic force and a size of the perforation 90 is decreased (S20).

After the towing devices 1 for endoscopy to which the magnetic materials are coupled are attached to the body tissues 70 located at the periphery of the perforation 90, the towing devices 1 for endoscopy are pulled using pincers of the endoscope to cause the extension portions 40 made of magnetic materials to come into contact with each other. Alternatively, inner air is suctioned through a suction operation of the endoscopes so that organs shrink and thus two extension portions 40 closely approach and come into contact with each other.

As illustrated in FIGS. 10, 11, and 20, a plurality of clip portions 30 are installed at a portion in which a size of the perforation 90 is decreased, and the body tissues 70 in which the perforation 90 is formed are sutured (S30).

Through the above process, the perforation 90 is divided into a first perforation 92 having a small diameter and a second perforation 94 centered on the towing devices 1 for endoscopy to which the magnetic materials are attached. The body tissues 70 pulled by the extension portions 40 made of the magnetic materials are additionally sutured using general clip portions 30.

In addition, as illustrated in FIGS. 12 and 20, the extension portions 40 are removed and the suture is completed (S40).

The extension portions 40 made of the magnetic materials and the towing devices 1 for endoscopy to which the extension portions 40 are coupled have to be removed from an inside of a human body using a foreign body removal forceps so that the human body is not harmed. In addition, a magnetic force of the extension portion 40 made of a magnetic material may be adjusted by adjusting a size of the extension portion 40.

A suturing procedure of the perforation 90 using the endoscope becomes easy through the present invention, and a suturing procedure of the perforation 90 having a large diameter may be performed more easily than a conventional technique. Since a suturing technique using the endoscope is developed, the suturing technique using the endoscope can also be applied as a more effective suturing technique in place of laparotomy for which treatment and recovery are slow. A large suture with which it is difficult to perform suturing using an existing technique or that requires use of other tools can be performed through the suturing technique using the endoscope. In addition, even though a large number of clip portions 30 are used to suture in a conventional suturing technique, the present invention can be used to decrease the number of used clip portions 30 through an initial suture using the magnetic material.

Figure 13:
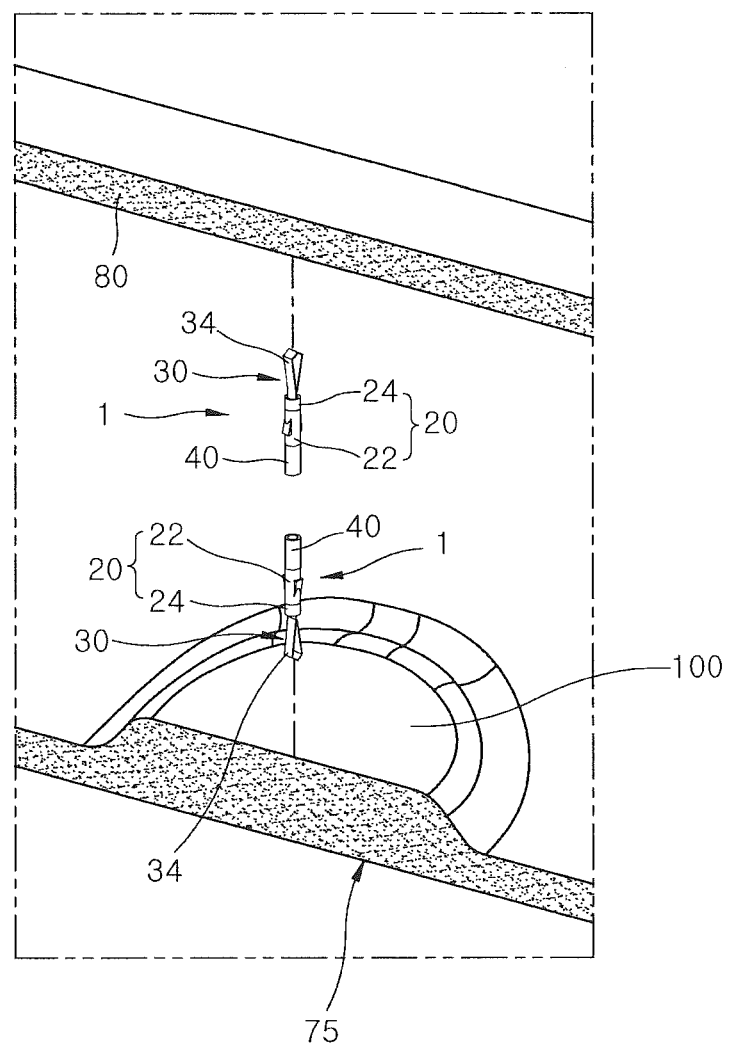
FIG. 13 is a perspective view illustrating a state in which the towing devices for endoscopy are positioned in front of first body tissues having an internal lesion and second body tissues facing the first body tissues.
Figure 14:
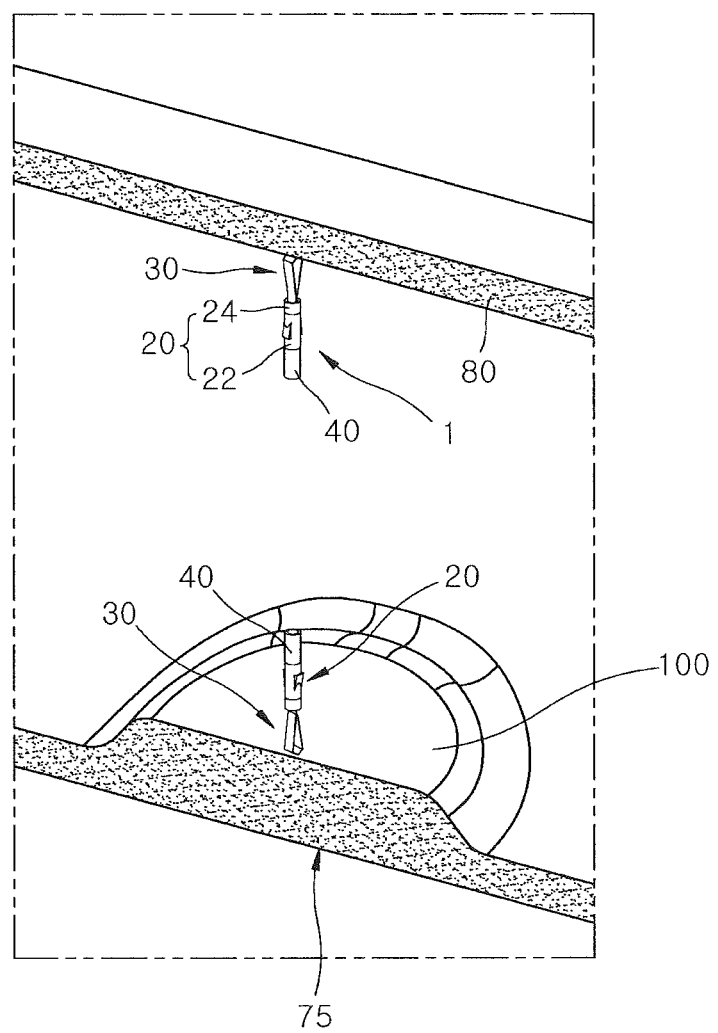
FIG. 14 is a perspective view illustrating a state in which the towing devices for endoscopy are installed at the first body tissues and the second body tissues.
Figure 15:
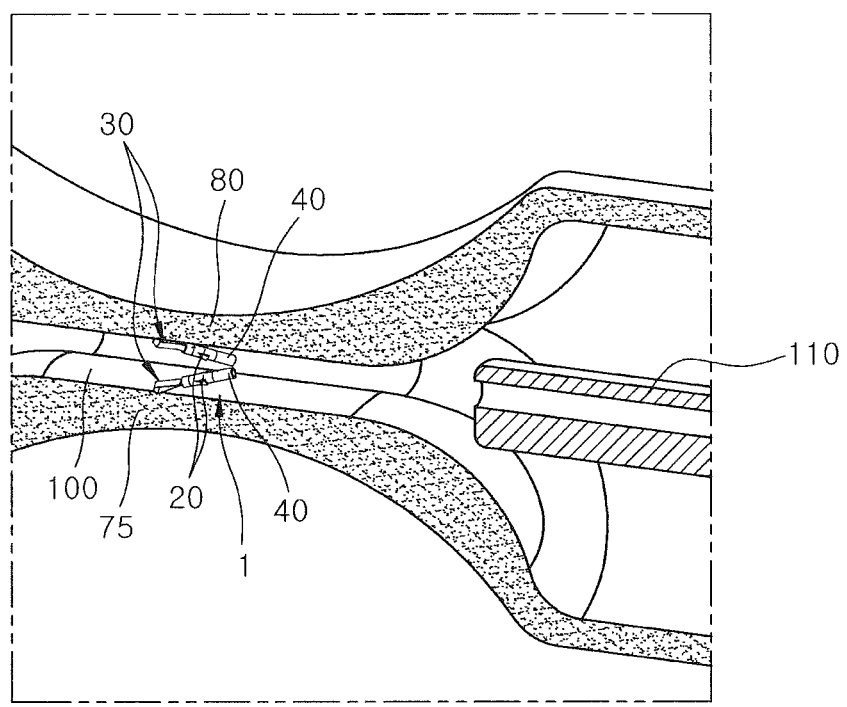
FIG. 15 is a perspective view illustrating a state in which the extension portions of the upper and lower towing devices are brought into contact with each other after a suction operation between the first body tissues and the second body tissues is performed.
Figure 17:
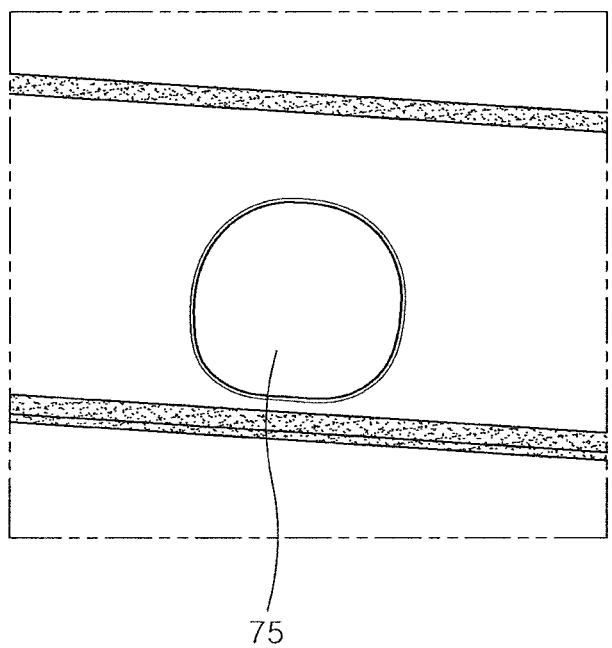
FIG. 17 is a perspective view illustrating a state in which the towing devices for endoscopy are removed from the first body tissues and the second body tissues after the internal lesion is removed.
Figure 21:
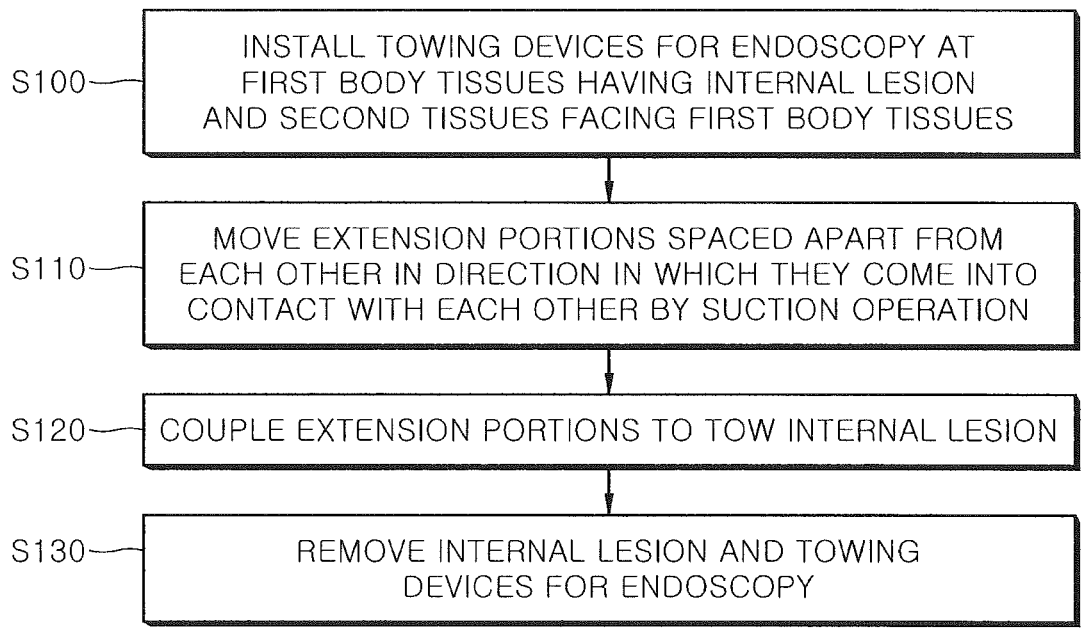
FIG. 21 is a flowchart of a towing method using a towing device for endoscopy according to another embodiment of the present invention.

FIG. 13 is a perspective view illustrating a state in which the towing devices for endoscopy are positioned in front of first body tissues having an internal lesion and second body tissues facing the first body tissues, FIG. 14 is a perspective view illustrating a state in which the towing devices for endoscopy are installed at the first body tissues and the second body tissues, FIG. 15 is a perspective view illustrating a state in which the extension portions of the upper and lower towing devices are brought into contact with each other after a suction operation between the first body tissues and the second body tissues is performed, FIG. 16 is a perspective view illustrating a state in which the first body tissues having the internal lesion are towed toward the second body tissues, FIG. 17 is a perspective view illustrating a state in which the towing devices for endoscopy are removed from the first body tissues and the second body tissues after the internal lesion is removed, and FIG. 21 is a flowchart of a towing method using a towing device for endoscopy according to another embodiment of the present invention.

As illustrated in FIGS. 13, 14, and 21, a towing method using the towing device 1 for endoscopy according to another embodiment of the present invention includes the installing towing devices 1 for endoscopy having the clip portions 30 configured to grip a target object and the extension portions 40 having magnetic forces at first body tissues 75 having an internal lesion 100 and second body tissues 80 facing the first body tissues 75 (S100).

The clip portion 30 of the towing device 1 for endoscopy including the extension portion 40 is fixed to a portion to be towed such as a portion at which incision is needed due to the internal lesion 100, and the clip portion 30 of the towing device 1 for endoscopy including the extension portion 40 is also fixed to the second body tissues.

As illustrated in FIGS. 15 and 21, a suction operation is performed between the first body tissues 75 and the second body tissues 80, and the first body tissues 75 and the second body tissues 80 at which the towing devices 1 for endoscopy are installed are moved in a direction to come into contact with each other (S110).

The extension portions 40 made of magnetic materials and positioned at one ends of two towing devices 1 for endoscopy are connected to each other. Two extension portions 40 are attached to each other using a forceps, or sizes of the organs are decreased by decreasing an internal pressure using a suction portion 110. Since a distance between the two magnets is decreased through such an operation, the two extension portions 40 are attached to each other by the magnetic forces.

As illustrated in FIGS. 16 and 21, the extension portions 40 connected to the first body tissues 75 and the second body tissues 80 are coupled to each other by magnetic forces, and the first body tissues 75 having an internal lesion 100 moves toward the second body tissues 80 (S120).

As illustrated in FIGS. 16 and 17, a surgical procedure such as endoscopic submucosal dissection (ESD) is performed at a portion under the internal lesion 100 lifted upward.

The internal lesion 100 is removed, and the towing devices 1 for endoscopy connected to the first body tissues 75 and the second body tissues 80 are removed (S130).

Peeling and resection procedures using the endoscope may be performed more quickly and accurately through the present invention. Since the internal lesion 100 is already towed, there are various advantages in securing a view, checking an interface, and the like. In addition, since a procedure may be performed using the endoscope having one channel in place of a conventional method through which the same procedure is performed using an endoscope having two channels, procedure cost and time can be decreased.

Figure 22:
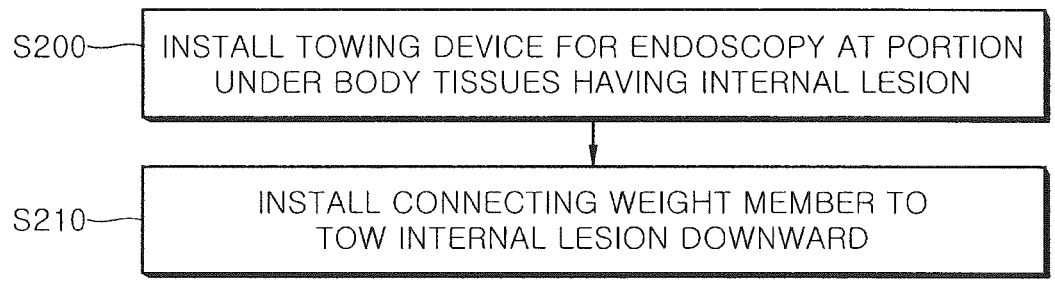
FIG. 22 is a flowchart of a towing method using a towing device for endoscopy according to still another embodiment of the present invention.

FIG. 22 is a flowchart of a towing method using a towing device for endoscopy according to still another embodiment of the present invention.

As illustrated in FIGS. 18 and 22, a towing method using the towing device 1 for endoscopy according to still another embodiment of the present invention includes installing the towing device 1 for endoscopy having the clip portion 30 configured to grip a target object and the extension portion 40 having a magnetic force at body tissues 72 having an internal lesion 100 (S200).

As illustrated in FIGS. 19 and 22, the connecting weight member 50 is connected to the extension portion 40 to tow the body tissues 72 having an internal lesion 100 downward (S210).

The connecting weight member 50 is attached to the extension portion 40 made of a magnetic material so that a tension is applied to a mucous membrane by gravitation, and a periphery of the elongated internal lesion 100 is incised.

The towing device 1 for endoscopy according to one embodiment of the present invention is used for a method for towing a region greater than a region which is towed during a surgical procedure using only a conventional clip portion 30, and may perform a towing operation using a magnetic material during an endoscopy. Through such a method, a tool does not become much more complex than that used in a conventional technique and may tow an organ in a wide region.

As described above, since the clip portion 30 configured to grip the body tissues 70 and the extension portion 40 having the magnetic force are integrally connected to each other, and the extension portions 40 come into contact with each other in a state in which the clip portions 30 grip the body tissues 70, an initial towing operation of the body tissues 70 can be easily performed.

As described above, in a towing device for endoscopy according to one embodiment of the present invention, since a clip portion configured to grip body tissues is integrally connected to an extension portion having a magnetic force, and extension portions come into contact with each other in a state in which clip portions grip the body tissues, an initial towing operation of the body tissues can be facilitated.

While the present invention has been described with reference to the embodiments illustrated in the drawings, these are only examples. It may be understood by those skilled in the art that various modifications and other equivalent embodiments may be made. Therefore, the scope of the present invention is defined by the appended claims and encompasses equivalents that fall within the scope of the appended claims.

What is claimed is:
1. A towing device for endoscopy comprising:
   a connecting portion connected to a wire of an endoscope to be moved and having an area with a reduced diameter;
   a guide portion including an inner path through which the connecting portion moves;
   a clip portion positioned in front of the guide portion and located on the opposite side of the wire and linked to the connecting portion to be folded and grip body tissues;
   an extension portion configured to move together with the guide portion and having a magnetic force; and
   a connecting weight member detached from or attached to the extension portion, and configured to tow the clip portion and the body tissues together with the extension portion downward due to a weight of the connecting weight member,
wherein the connecting weight member includes iron or a magnet and is coupled to the extension portion by a magnetic force.

2. The towing device for endoscopy of claim 1, wherein the connecting portion includes:
a first body connected to the wire;
a second body connected to the clip portion; and
a breaking body configured to connect the first body and the second body and having an area with a reduced diameter.

3. The towing device for endoscopy of claim 1, wherein:
the guide portion and the extension portion are formed in a pipe shape; and
the connecting portion sequentially passes through insides of the extension portion and the guide portion and is connected to the clip portion.

4. The towing device for endoscopy of claim 3, wherein both sides in a longitudinal direction of the extension portion have different magnetic polarities from each other.

5. The towing device for endoscopy of claim 3, wherein the extension portion includes a permanent magnet.

6. The towing device for endoscopy of claim 1, wherein the clip portion includes:
a linking hook linked to the connecting portion and having a hook shape; and
a grip portion configured to extend from the linking hook and open in a pincers shape, and drawn into the guide portion so that both ends spaced apart from each other come toward each other.

7. The towing device for endoscopy of claim 1, wherein:
a hole into which the extension portion is inserted is formed in the connecting weight member; and
the extension portion made of a magnetic material is inserted into the connecting weight member and is connected to the connecting weight member.

8. The towing device for endoscopy of claim 7, wherein the connecting weight member is connected to the extension portion to tow body tissues having an internal lesion downward.

* * * * *